United States Patent [19]

Lee et al.

[11] Patent Number: 5,612,341
[45] Date of Patent: Mar. 18, 1997

[54] BROMINATED HEXAHYDROXYBIPHENYL DERIVATIVES

[75] Inventors: Kuo-Hsiung Lee, Chapel Hill, N.C.; Yoshiki Kashiwada, Niigata, Japan; Lan Xie, Chapel Hill, N.C.; Louis M. Cosentino, Springfield, Va.; Mark Manak, Laurel, Md.; Jing-Xi Xie, Beijing, China; Yung-Chi Cheng, Woodbridge, Conn.; Robert Kilkulskie, Shrewsbury, Mass.

[73] Assignees: Biotech Research Laboratories, Rockville, Md.; University of North Carolina at Chapel Hill, Chapel Hill, N.C.

[21] Appl. No.: 477,939

[22] Filed: Jun. 7, 1995

[51] Int. Cl.$^6$ .................. A61K 31/36; C07D 317/62; C07D 317/64; C07D 317/66

[52] U.S. Cl. .................. 514/253; 514/422; 514/464; 514/466; 544/377; 548/526; 549/435

[58] Field of Search .................. 549/435; 548/526; 544/377; 514/464, 466, 422, 253

[56] References Cited

U.S. PATENT DOCUMENTS

| | | | |
|---|---|---|---|
| 4,849,448 | 7/1989 | Kimura et al. | 514/464 |
| 4,868,207 | 9/1989 | Shi-jie | 514/464 |
| 4,904,694 | 2/1990 | Matsuoka et al. | 514/464 |
| 4,987,240 | 1/1991 | Matsuoko et al. | 549/436 |
| 4,996,331 | 2/1991 | Kimura et al. | 549/229 |
| 5,103,023 | 4/1992 | Iwasaki et al. | 549/350 |
| 5,159,069 | 10/1992 | Hirayama et al. | 536/118 |
| 5,182,404 | 1/1993 | Iwasaki et al. | 548/237 |
| 5,233,057 | 8/1993 | Iwasaki et al. | 549/435 |
| 5,264,594 | 11/1993 | Kimura et al. | 549/436 |

FOREIGN PATENT DOCUMENTS

| | | |
|---|---|---|
| WO90/04968 | 5/1990 | WIPO . |
| WO94/14763 | 7/1994 | WIPO . |

OTHER PUBLICATIONS

Cardellina, J.H., II, et al., "A Chemical Screening Strategy for the Dereplication and Prioritization of HIV–Inhibitory Aqueous Natural Products Extracts," *J. Natural Prod.* 56(7):1123–1129 (Jul. 1993).

Gengtao, L., "Hepato–Pharmacology of *Fructus schizandrae*," in: *Advances in Chinese Medicinal Materials Research*, Chang, H.M., et al., Eds., Singapore: World Scientific Publ. Co., pp. 257–267 (1985).

Kakiuchi, N., et al., "Inhibitory Effect of Tannins on Reverse Transcriptase from RNA Tumor Virus," *J. Natural Prod.* 48(4):614–621 (1985).

Kashiwada, Y., et al., "New Hexahydroxydiphenyl Derivatives as Potent Inhibitors of HIV Replication in H9 Lymphocytes," *Bioorg. Med. Chem. Letts.* 2(3):235–238 (1992).

Kashiwada, Y., et al., "New Hexahydroxybiphenyl Derivatives as Inhibitors of Protein Kinase C," *J. Med. Chem.* 37(1):195–200 (Jan. 7, 1994).

Nakashima, H., et al., "Inhibition of Human Immunodeficiency Viral Replication by Tannins and Related Compounds," *Antiviral Res.* 18:91–103 (1992).

Nonaka, G.–I., et al., "Anti–AIDS Agents, 2: Inhibitory Effects of Tannins on HIV Reverse Transcriptase and HIV Replication in H9 Lymphocyte Cells," *J. Natural Prod.* 53(3):587–595 (1990).

Okuda, T., et al., "Ellagitannins as Active Constituents of Medicinal Plants," *Planta Medica* 55:117–122 (1989).

Yi et al. (CA 108:204530f), 1988.

Huff, J. Med. Chem. vol. 34, No. 8, Aug. 1991, pp. 2305–2314.

*Primary Examiner*—Johann Richter
*Assistant Examiner*—Laura L. Stockton
*Attorney, Agent, or Firm*—Sterne, Kessler, Goldstein & Fox, P.L.L.C.

[57] ABSTRACT

Disclosed herein are derivatives of 4,4'-dimethoxy-5,6,5'6'-bimethylenedioxy 2,2'-dimethoxycarbonyl biphenyl (DDB) which were synthesized and found to have anti-HIV activity. Of the compounds studied, 3,3'-dibromo DDB and 3-bromo-DDB initially exhibited the greatest anti-HIV activity.

20 Claims, 5 Drawing Sheets

SCHEME 1

FIG.4

SCHEME 2

FIG.5

BROMINATED HEXAHYDROXYBIPHENYL DERIVATIVES

FIELD OF THE INVENTION

The present invention relates to compounds which have been found to be useful in treating viral infections, such as HIV infections.

BACKGROUND OF THE INVENTION

Retroviruses

Retroviruses are small, single-stranded positive-sense RNA viruses. A retroviral particle comprises two identical single-stranded positive sense RNA molecules. Their genome contains, among other things, the sequence of the RNA-dependent DNA polymerase, also known as reverse transcriptase. Many molecules of reverse transcriptase are found in close association with the genomic RNA in the mature viral particles. Upon entering a cell, this reverse transcriptase produces a double-stranded DNA copy of the viral genome, which is then inserted into the chromatin of a host cell. Once inserted, the viral sequence is called a provirus. Retroviral integration is directly dependent upon viral proteins. Linear viral DNA termini (the LTRs) are the immediate precursors to the integrated proviral DNA. There is a characteristic duplication of short stretches of the host's DNA at the site of integration.

Progeny viral genomes and mRNAs are transcribed from the inserted proviral sequence by host cell RNA polymerase in response to transcriptional, regulatory signals in the terminal regions of the proviral sequence, the long terminal repeats, or LTRs. The host cell's protein production machinery is used to produce viral proteins, many of which are inactive until processed by virally encoded proteases. Typically, progeny viral particles bud from the cell surface in a non-lytic manner. Retroviral infection does not necessarily interfere with the normal life cycle of an infected cell or organism. However, neither is it always benign with respect to the host organism. While most classes of DNA viruses can be implicated in tumorigenesis, retroviruses are the only taxonomic group of RNA viruses that are oncogenic. Various retroviruses, such as the Human Immunodeficiency Virus (HIV), which is the etiological agent responsible for acquired immune deficiency syndrome (AIDS) in humans, are also responsible for several very unusual diseases of the immune system of higher animals.

HIV INFECTION AND AIDS

Human Immunodeficiency Virus (HIV) is a member of the lentiviruses, a subfamily of retroviruses. Many retroviruses are well-known carcinogens. HIV per se is not known to cause cancer in humans or other animals, but it does present a formidable challenge to the host. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., *Nature* 312:763–767, 1984). These interactions not only mediate the infection of susceptible cells by HIV, but are also responsible for the virus-induced fusion of infected and uninfected T. cells. This cell fusion results in the formation of giant multinucleated syncytia, cell death, and progressive depletion of CD4 cells in AIDS patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They can interact and fuse with CD4-bearing T cells, causing T cell depletion and thus contributing to the pathogenesis of AIDS.

ANTI-HIV DRUGS

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA, ddT, ddI, and ddC. These drugs inhibit the viral enzyme reverse transcriptase, thereby inhibiting de novo infection of cells. However, once viral infection has been established within a cell, viral replication utilizes host cell enzymes. Thus, drugs which inhibit only reverse transcriptase tend to have limited effects. While the spread of free virus within the organism can be blocked, the mechanisms of syncytia formation and pathogenesis through direct intercelluar spread remain. Accordingly, there is a need to provide new anti-HIV drugs which are not limited to inhibiting reverse transcriptase as their mechanism of action.

In an effort to find new and more effective drugs for treating HIV infections, attention has turned to compounds found in plants or compounds modified from natural products. In particular, tannins have been investigated for their medicinal uses, and several elagitannins exhibit some anti-tumor and anti-HIV activity (Okuda et al., *Planta Med.* 55:(2) 117–122, 1989; Bokesch et al., *J. Nat Prod.* 56(7): 1123–1129, 1993). Unfortunately, reports of the inhibition of reverse transcriptase of the tannins show that many of these tannins have little or no activity against reverse transcriptase, and there is as yet no reliable means for predicting which of these compounds will be effective (Kakiuchi et al., *J. Nat. Prod.* 48(4): 614–621, 1985; Nonaka et al., *J. Nat. Prod.* 53(3):587–595, 1990; Nakashima et al., *Antiviral Res.* 18(1): 91–103, 1992; Weaver et al., *Biochem Pharmacol.* 43(11): 2479–2489, 1992; Kilkuskie et al., *Bioorg. Med. Chem. Lett.* 2(12): 1529–1534, 1992).

Many of the tannin-based compounds are biphenyl derivatives. Historically, biphenyl derivatives have been investigated for their utility in treating a variety of liver diseases. One anti-viral agent has been used for the treatment of hepatitis in China (Liu et al., Hepato-pharmacology of *Fructus Schizandrae* in Advances in Chinese Medical Materials Research, edited by Chang et al., pp 257–267). One compound disclosed therein, 4,4'-dimethoxy-5,6,5'6'-bimethylenedioxy-2,2'- dimethoxycarbonyl biphenyl (DDB), exhibited some anti-HIV activity, with an ED50 value of 5 microgram/ml and a TI of >20.

*Schinsandra chinensis* (Chinese name: Wu-Wei-Zi) has long been used in China as an astringent and tonic. In the

1970's it was found to be effective against viral hepatitis, for lowering elevated SGPT levels, and as a protective agent for the liver when injured by chemical agents such as carbon tetrachloride. Further study indicated that schisandrin C, isolated from the seeds of *Schinsandra chinensis*, was an active principle. During the total synthesis of schisandrin C, a new anti-hepatic drug, 4,4'-dimethoxy-5,6,5'6,-bimethylenedioxi-2,2'-dimethoxycarbonyl biphenyl was discovered.

Shi-jie, in U.S. Pat. No. 4,868,207, discloses bis(methylenedioxy)biphenyl compounds of the formula wherein R is an alkyl group having 1 to 6 carbon atoms or a phenyl group, and R' is a hydrogen atom or an alkyl group of 1 to 6 carbon atoms.

Iwasaki et al., in U.S. Pat. Nos. 5,103,023; 5,182,404 and 5,233,057; disclose biphenyl derivatives of the formula:

wherein $R^1$ is a substituted or unsubstituted aminocarbonyl group, aminothiocarbonyl group, a substituted or unsubstituted lower alkoxycarbonyl group, cyano group, or a group of the formula:

one or two of $R^2$ to $R^7$ are hydrogen, and the remaining groups are the same or different and are each a lower alkoxy group, a phenyl(lower) alkoxy group or hydroxy group, or the adjacent two groups thereof combine to form a lower alkylenedioxy group, and $Alk^1$ is a lower alkylene group, or a pharmaceutically acceptable salt thereof, which are useful for the prophylaxis and treatment of hepatic diseases.

Example 19 discloses 5,6,5',6'-dimethylenedioxy-2,2'-biphenylbis(thiocarboxamide), which is the only compound in this group with two dimethylenedioxy groups on the biphenyl derivative.

Kimura et al., in U.S. Pat. Nos. 4,849,448; 4,996,331; and 5,264,594; disclose biphenyl derivatives which can be used to treat hepatitis. The biphenyl derivative has the formula:

wherein $R_0$ and $R_1$ independently stand for a lower alkyl group or $R_0$ and $R_1$ together represent a group O=C<, $R_2$ stands for an alkyl group having 1 to 3 carbon atoms, and $R_3$ and $R_4$ independently stand for a hydrogen atom or a lower alkyl group.

Matsuoka et al., in U. S. Pat. Nos. 4,904,694 and 4,987,240, disclose biphenyl derivatives which are used for moderating liver ailments and for treating hepatitis. These compounds have the formula:

wherein $R_1$ and $R_2$ stand for hydrogen or methyl.

Hirayama et al., U.S. Pat. No. 5,159,069, disclose sulfated tannins which have antiviral activity and reverse transcriptase inhibition which can be used to treat patients infected with viruses such as HIV.

Citation of documents herein is not intended as an admission that any of the documents cited herein is pertinent prior art, or an admission that the cited document is considered material to the patentability of the claims of the present application. All statements as to the date or representation as to the contents of these documents is based upon the information available to the applicant, and does not constitute any admission as to the correctness of the dates or contents of these documents.

SUMMARY OF THE INVENTION

The present invention is intended to overcome one or more deficiencies of the related art.

The present invention is also intended to provide compounds which have anti-viral activity and/or antiretroviral activity, such as anti-HIV activity, in vitro, in situ, and/or in vivo, as well as preparing these compounds.

The present invention produces biphenyl derivatives which can be used to inhibit retroviral growth, replication, binding and/or metabolism, and/or to treat a retroviral infection or related symptoms.

The present invention also provides a process for preparing biphenyl derivatives.

The compounds of the present invention have the following formula:

wherein $R^1$ and $R^2$ are hydrogen or bromine, with the proviso that at least one of $R^1$ or $R^2$ is bromine; $R^3$ and $R^4$ are OH, O—$C_{1-6}$ alkyl, $O(CH_2)_2N^+(CH_3)_3Cl^-$, In particular, compounds having the most potent anti-HIV activity are:
3-bromo-4,4'-dimethoxy-5,6,5'6'-bimethylenedioxy-2,2'-dimethoxycarbonyl biphenyl and
3,3'-dibromo-4,4'-dimethoxy-5,6,5'6'-bimethylenedioxy-2,2'-dimethoxycarbonyl biphenyl.

The invention is also directed to a method for treating a subject infected with HIV-1 by administering at least one of the above-noted compounds, optionally in combination with any one or more of the known anti-AIDS therapeutics or an immunostimulant.

The treatment methods of the present invention also include administering to a subject infected with HIV-1 a conjugate of a compound as described above with soluble CD4, CD4 derivatives, antibodies specific for CD4, or HIV-coded glycoproteins such as gp120 and gp41, or antibodies thereto.

Other features, advantages, embodiments, aspects and objects of the present invention will be clear to those skilled in the areas of relevant art, based upon the description, teaching and guidance presented herein.

DETAILED DESCRIPTION OF THE PREFERRED EMBODIMENTS

The present invention relates to which compounds have been discovered to be useful in inhibiting retroviral infection and/or replication in eukaryotic cells and/or for the treatment of retroviral infections, such as HIV infection, as well as to methods of preparing the compounds.

Derivatives of 4,4'-dimethoxy-5,6,5'6'-bimethylenedioxy-2,2'-dimethoxy carbonyl biphenyl (3, DDB) were synthesized and evaluated for their inhibitory activity against HIV-1 replication in acutely infected H9 cells. Four compounds of the derivatives prepared demonstrated particularly potent anti-HIV activity with $EC_{50}$ values of <0.8 and 0.3 μg/ml and therapeutic index values of >100 and >333, respectively. A comparison of the anti-HIV activity of these compounds suggested that the types of substituents on the phenolic hydroxy groups as well as the presence of at least one bromine substituent rather than the number of bromine(s) on the aromatic rings are important to the enhanced anti-HIV activity. The compounds of the present invention also exhibited potent inhibitory activity against HIV-1 reverse transcriptase in a template-primer dependent manner.

The compounds of the present invention have been unexpectedly discovered to have anti-retroviral activity, thus providing suitable compounds and compositions for treating retroviral infections, optionally with additional pharmaceutically active ingredients, such as anti-retroviral, anti-HIV, and/or immuno-stimulating compounds or antiviral antibodies or fragments thereof.

By the term "anti-retroviral activity" or "anti-HIV activity" is intended the ability to inhibit at least one of:

(1) retroviral attachment to cells;

(2) viral entry into cells;

(3) cellular metabolism which permits viral replication;

(4) inhibition or intercellular spread of the virus;

(5) synthesis and/or cellular expression of viral antigens;

(6) activity of virus-coded enzymes (such as reverse transcriptase and protease); and/or (7) any known retroviral or HIV pathogenic actions, such as, for example, immunosuppression. Thus, any activity which tends to inhibit any of these mechanisms is "anti-retroviral activity" or "anti-HIV activity."

Synthesis

DDB (4,4'-dimethoxy-5,6,5'6'-dimethylenedioxy-2,2'-dimethoxycarbonyl biphenyl (compound 3 in Scheme 1) was synthesized according to the procedure of Xie et al., *Acta Pharmaceutica sinica* 17:23–27, 1982). As shown in Scheme 1, DDB was treated with one and two molar equivalents of bromine in $CHCl_3$ to yield the mono-(4) and di-(5)bromide, respectively. Compound 5 resisted subsequent hydrolysis with base, probably due to the steric hindrance of the bulky bromine atoms ortho to the hydroxy groups. Hydrolysis was achieved using relatively strong conditions to yield the dicarboxylic acid (6). Compound 6 was treated with acetic anhydride to give an intramolecular anhydride (8). Treatment of 8 with alcohol yielded the monoester (9), while reaction with amines furnished monoamides (12 and 13). The water-soluble trimethylamino carboxylate salt (11) was obtained by treating 8 with choline chloride in pyridine. Reaction of 8 with amines furnished monoamides (12 and 13). Similar treatment of 8 with 1-(2hydroxyethyl)pyrrolidine, however, yielded a dicarboxylic acid salt (14). In its $^1H$ NMR spectrum, compound 14 showed the presence of two pyrrolidinium ethanol moieties [δ1.95 (8H,m), 3.19 (4H, t, J=5 Hz), 3.26 (8H,m), 3.75(4H, t,J=5 Hz)], along with the signals due to two methoxy [δ3.9 (6H, s)] and two methylenedioxy [δ5.83 and 5.88 (each 2H, s)] groups. The chemical shift [δ3.75 (4H, t, J=5 Hz)] of the hydroxymethyl groups of the pyrrolidinium ethanol moieties suggested that these positions were not esterified. In addition, the IR spectrum of 14 did not exhibit extra carbonyl absorption around 1700 cm$^{-1}$, but instead showed absorption bands due to a carboxylate (1580 and 1370 cm$^{-1}$), indicating that 14 is the dipyrrolidinium ethanol salt of 6. Treatment of 6 with 1-hexanol under acidic conditions yielded the corresponding diester 15. Compounds 6 and 9 were treated with appropriate molar equivalents to furnish di-(7) and mono-(10) sodium salts.

Similar mono-(16 and 18) and di-(17 and 19) bromo derivatives of previously reported biphenyl compounds (Kashiwada et al., Bioorg., Med. Chem. Lett, 2:234–238, 1992; Kashiwada et al., J. Med. Chem. 37: 195–200, 1994) were also prepared by the procedure described above.

DDB has three different groups in each benzyl ring, and a series of isomers can be obtained by changing the relative position of these groups. During the total synthesis of DDB from gallic acid as the starting material, two isomers, 6,6'-dimethoxy- 4,5,4'5'-bimethylenedioxy-2,2'-dimethoxycarbonyl biphenyl (114) and 4,6'-dimethoxy-5,6,4'5'-binethylenedioxy,2,2'-dimethoxycarbonyl biphenyl (115) were both obtained in the Ullmann reaction. Additional isomers of DDB, 116 and 117, were synthesized according to the route shown in Scheme 11.

The starting material, 2,3,4-trihydroxybenzoic acid, was first esterified to give methyl 2,3,4-trihydroxybenzoate 120. The monoethylation of the 4-OH group in compound 120 was achieved by Scheline's method. The IR spectra of the product showed the absorption peak of the ester carbonyl group at 1660 cm$^{-1}$, indicating the presence of internal hydrogen bonding. In its $^1$H NMR spectra, a signal was observed at δ10.98 ppm, ascribable to the chelated OH group. These spectroscopic data indicated that monomethylation occurred at the 4-OH group, not at the 2-position. Thus, the structure of the monomethyl ether of compound 120 was assigned as methyl 2,3-dihydroxy-4-methoxybenzoate 121. Methylenation of compound 121 with CH$_2$Cl$_2$ in DMF afforded methyl 2,3-methylendioxy-4-methyoxbenzoate 122 in good yield (19%),. The IR absorption bands of the ester carbonyl group in 122 shifted from 1660 cm$^{-1}$ to 1710-cm$^{-1}$. Bromination of compound 122 with dioxanedibromide reagent in ethylene oxide yielded methyl 2,3-methylendioxy-4-methoxy-5-bromobenzoate 123 in good yield (>80%). The brominated compound 123 was also obtained by reacting compound 122 with dry bromine in CHCl$_3$. The position of the bromine atom introduced was determined unequivocally on the basis of a 2D-NOE spectrum. A strong NOE response was observed between the aromatic proton and the methyl protons of the methoxycarbonyl group. Therefore, bromination must have taken place at the 5-position, which was in accordance with the expected orientation for electrophilic aromatic substitution. Ullmann reaction of compound 123 with active copper powder in DMF gave only a very small amount of the biphenyl derivative 117. This compound gave a molecular ion at m/z 418 as the base peak in its MS spectrum. The IR and $^1$H NMR spectra agreed well with the assigned structure. The new compound 117 was named δ-DDB.

Four isomers of DDB (114–117) were now obtained via different pathways. The dibromination of three of these biphenyl compounds was readily accomplished at room temperature with a molar ratio of bromine to biphenyl of about 2:1. The structure of the dibrominated biphenyl derivatives 118, 119 and 110, prepared from 114, 115 and 116, respectively, were identified by their $^1$H NMR, MS, IR and EA data. However, compound 117 could not be brominated because of the effects of other functional groups in the biphenyl system.

Figure 4:
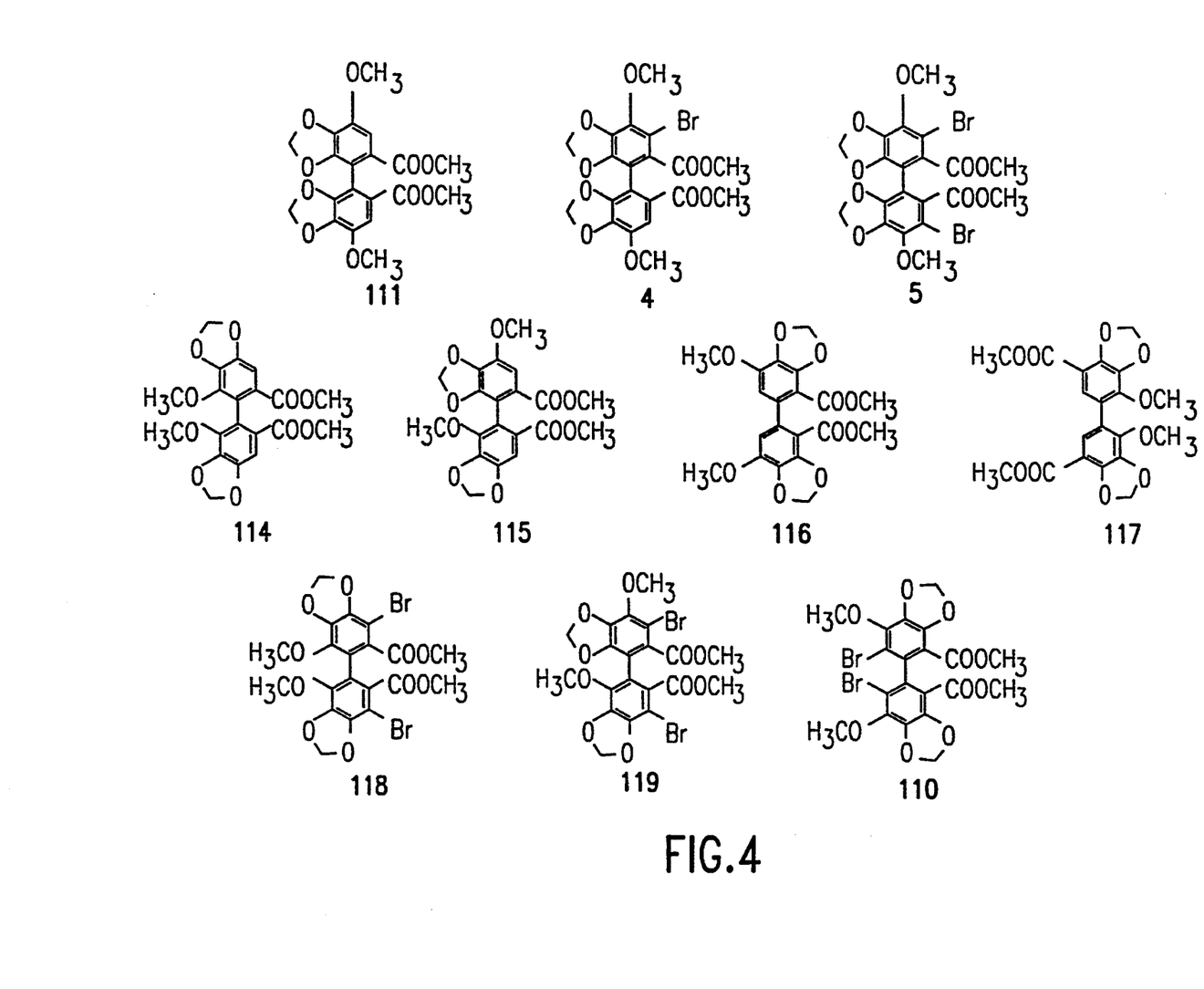
FIG. 4 illustrates compounds according to the present invention.
Figure 5:
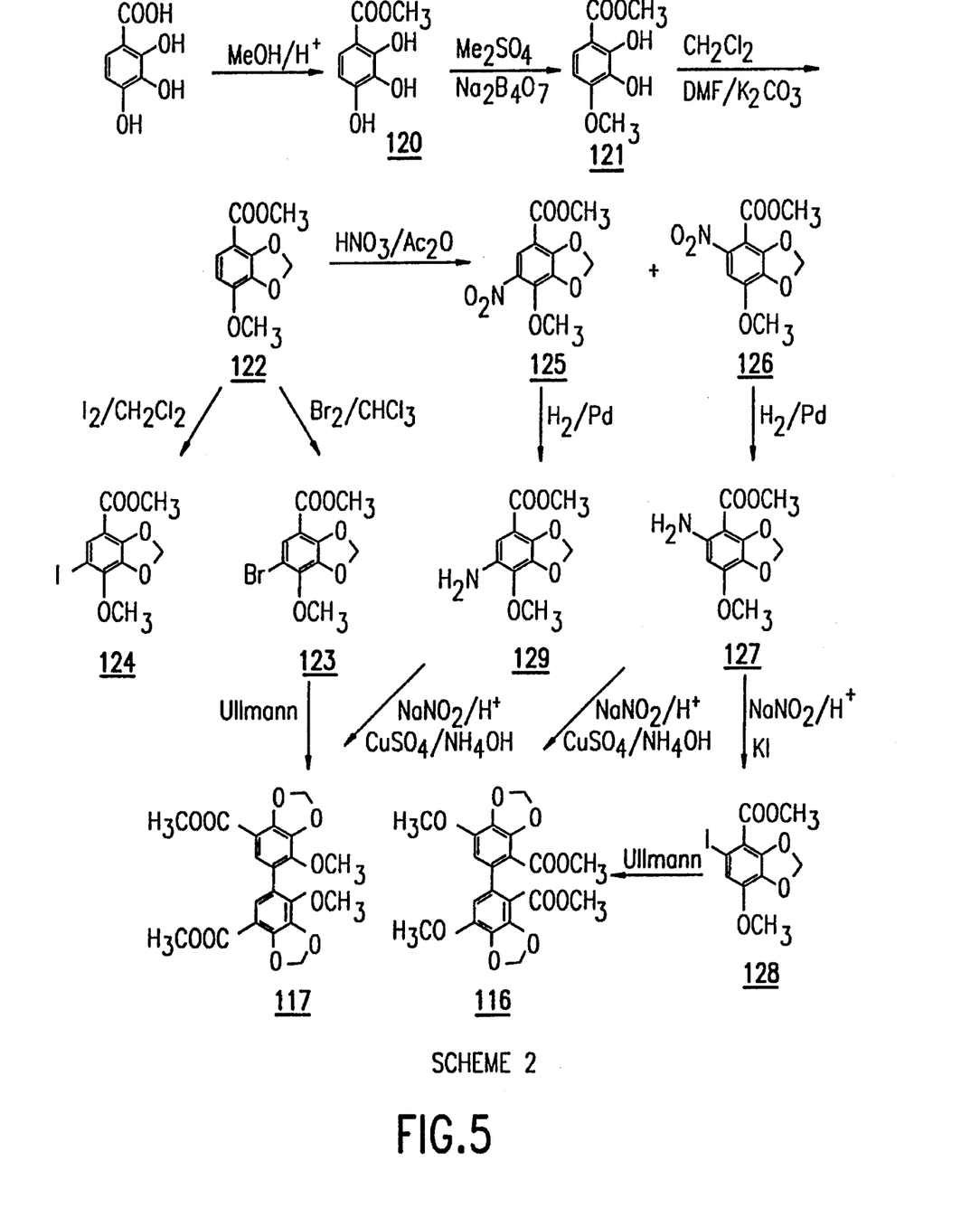
FIG. 5 is reaction scheme 2.

The anti-HIV activities of the biphenyl derivatives are shown in Table IA. Among these compounds, 3,3'-dibromo DDB (5) demonstrated potent anti-HIV activity with an EC$_{50}$ of 0.23 μg/mL and TI of >480. Comparison of the anti-HIV activities of compounds suggested that the relative position and types of substituents on the phenolic hydroxy groups rather than the numbers of bromine atoms on the aromatic rings are the most important. The 2- (or 2'-) methoxycarbonyl and 4- (or 4'-) methoxy groups on the biphenyl ring as found in compounds 111 and 115 composed an essential anti-HIV structural feature. Activity could then be enhanced greatly by a bromine introduced at the 3- or 3'-postion, as found in compounds 4, 5, and 119. Table IA shows this structure-activity relationship with an order of activity of 5>4>119>111>115 (based on FIG. 4). The other five compounds have no or less anti-HIV activity, regardless of the presence of bromine in the molecule. Therefore, the replacement of the methyl carboxylate groups at C-2 and C-2' or the methoxy groups at C-4 and C-4' by other groups led to a decrease in the anti-HIV activity.

Preliminary mechanism of action studies with compounds 4 and 5 have shown template-primer HIV-1 reverse transcriptase inhibitory activity. This type of inhibitory activity has also been observed for other non-nucleoside HIV reverse transcriptase inhibitors. Potent inhibitory effects were also found with 4 and 5 against HIV-1 reverse transcriptase-associated DNA polymerase and RNase II activities under certain conditions.

The structures of all of the biphenyl derivatives described above were confirmed by their spectral data and elemental analyses.

The anti-HIV activity of the biphenyl derivatives described above is shown in Tables I and IA. Among these compounds, 3,3'- dibromo DDB, compound 5, demonstrated potent anti-HIV activity with an EC$_{50}$ value of 0.23 μg/mL. It also exhibited a good therapeutic index of >480. Compound 4, 3bromo DDB, also showed potent anti-HIV activity, with EC$_{50}$ and TI values of 0.52 μg/mL and 190, respectively. Comparison of the anti-HIV activities of compounds 3–5 suggested that the number of bromine atoms on the aromatic rings might enhance anti-HIV activity. Therefore, compounds 16 and 17 were expected to be active, since compounds 4 and 16 and 5 and 17, respectively, are structurally similar to each other, except for the substitutents on the phenolic hydroxy groups. However, compounds 16 and 17 showed no anti-HIV activity in the tests conducted. Compounds 18 and 19 likewise showed no anti-HIV activity to date, although their parent compound (2) does possess anti-HIV activity [3,5], which is comparable to that of DDB.

Replacing the methyl carboxylate groups at C-2 and 2' by carboxylic acids (6,9), sodium carboxylates (7), alkylamino carboxylates (11) and alkylamino amides (12, 13) all led to a decrease in the anti-HIV activity of the compounds.

TABLE I

Anti-HIV Activities of Brominated Hexahydroxybiphenyl Derivatives in Acutely Infected H9 Lymphocytes

| | EC$_{50}$(μg/ml) | IC$_{50}$(μg/ml) | Therapeutic Index |
|---|---|---|---|
| 3 | 5 | >100 | >20 |
| 4 | 0.52 | >100 | >190 |
| 5 | 0.23 | >100 | >480 |
| 6 | >100 | >100 | 1 |
| 7 | >100 | >100 | 1 |

TABLE I-continued

Anti-HIV Activities of Brominated Hexahydroxybiphenyl Derivatives in Acutely Infected H9 Lymphocytes

|  | $EC_{50}$(μg/ml) | $IC_{50}$(μg/ml) | Therapeutic Index |
|---|---|---|---|
| 8 | — | >100 | — |
| 9 | 60 | >100 | >1.7 |
| 10 | — | >100 | — |
| 11 | >100 | >100 | 1 |
| 12 | 30 | >100 | >3.3 |
| 13 | >100 | >100 | 1 |
| 14 | 17 | >20 but <100 | >1.2 but <5.9 |
| 15 | 2 | >100 | >50 |
| 16 | >100 | >100 | 1 |
| 17 | >100 | >100 | 1 |
| 18 | 100 | >100 | >1 |
| 19 | >100 | >100 | 1 |

TABLE IA

Anti-HIV Activities of Isomers of DDB and Their Brominated Derivatives in Acutely Infected H9 Lymphocytes

| Compound Number | $IC_{50}$(μg/ml)[a] | $EC_{50}$(μg/ml) | Therapeutic Index[b] |
|---|---|---|---|
| 111 | >100 | 5 | >20 |
| 4 | 100 | 0.52 | 190 |
| 5 | >100 | 0.23 | >480 |
| 114 | >100 | 65 | >1.2 |
| 115 | >100 | 7.5 | >13 |
| 116 | >100 | 70 | >1.4 |
| 117 | 1.8 | no inhibition | — |
| 118 | >100 | 90 | >1.1 |
| 119 | >100 | 2.1 | >48 |
| 110 | 45 | no inhibition | — |

[a]$IC_{50}$ refers to the concentration of drug that causes a 50% reduction in total cell number. Drugs that have $IC_{50}$ values >100 μg/ml can not be tested at higher concentrations for a more exact $IC_{50}$ value due to the effect of the solvent, DMSO.
[b]Therapeutic Index (TI) is a ratio of the IC50 value/$EC_{50}$ value. Therefore, when the $IC_{50}$ value is >100 μg/ml (refer to a above), the TI value must also be reported as greater than.

Figure 1:
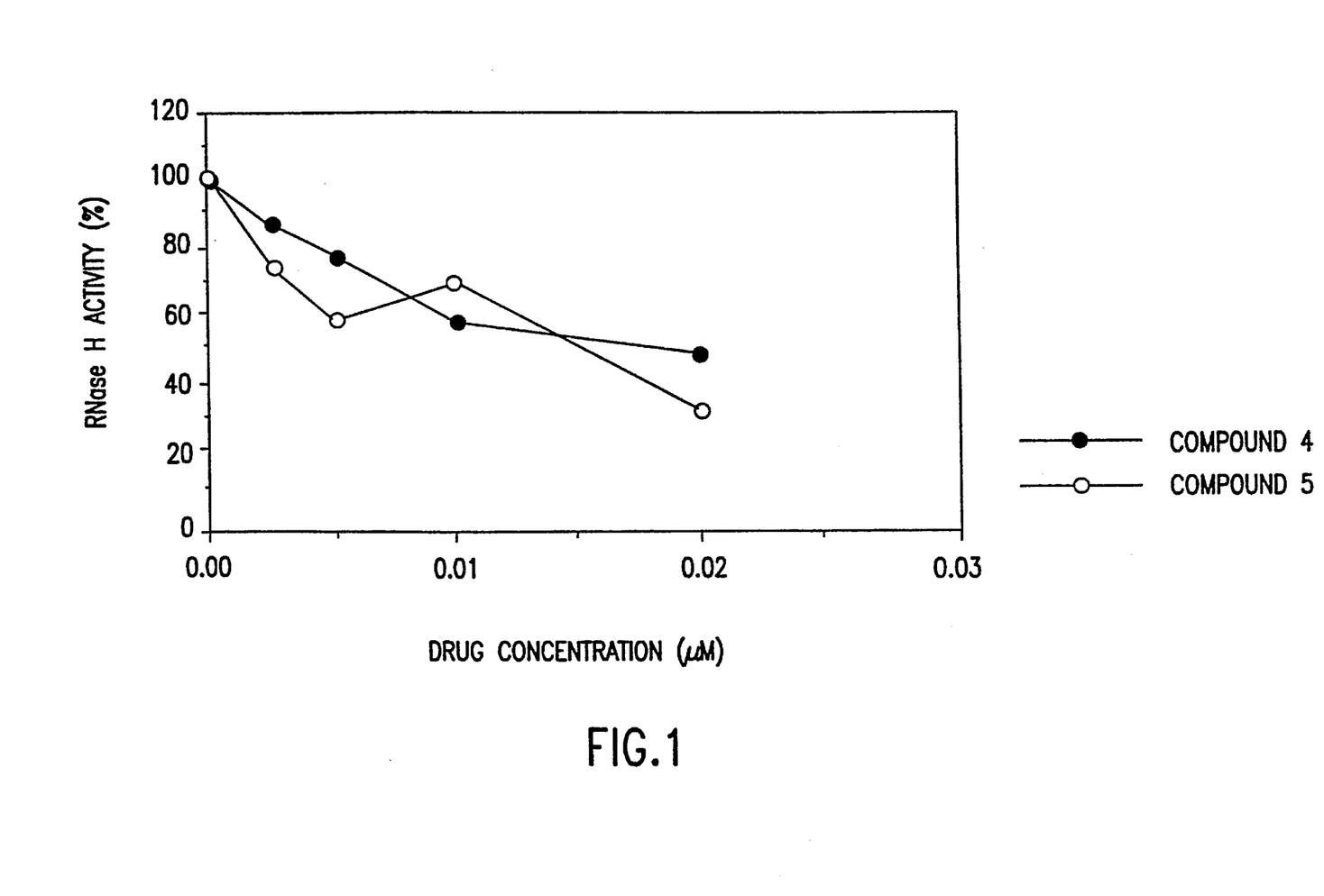
FIG. 1 shows inhibition of HIV reverse transcriptase associated RNase H activity by two compounds of the present invention.
Figure 2:
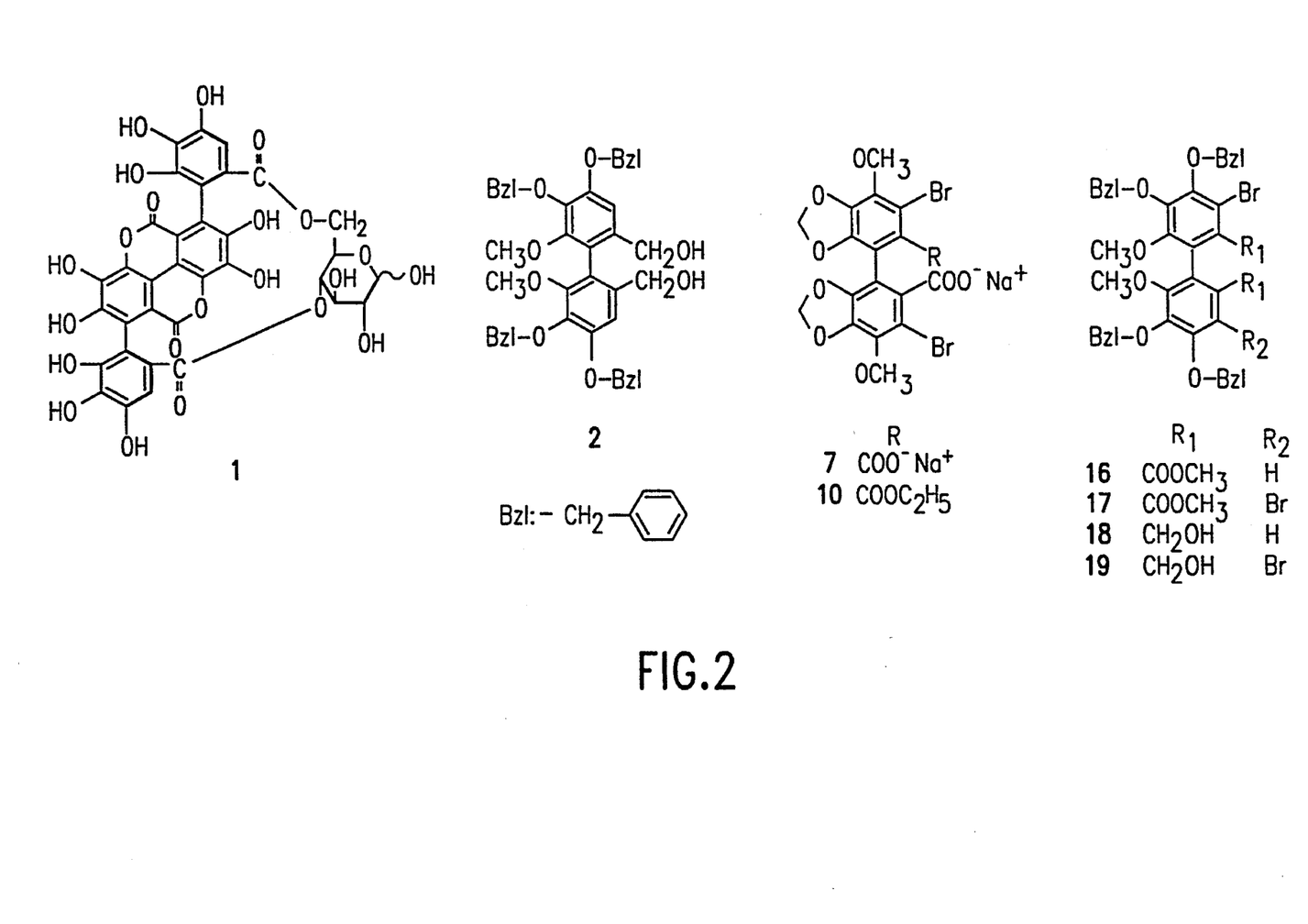
FIG. 2 illustrates compounds of the present invention.
Figure 3:
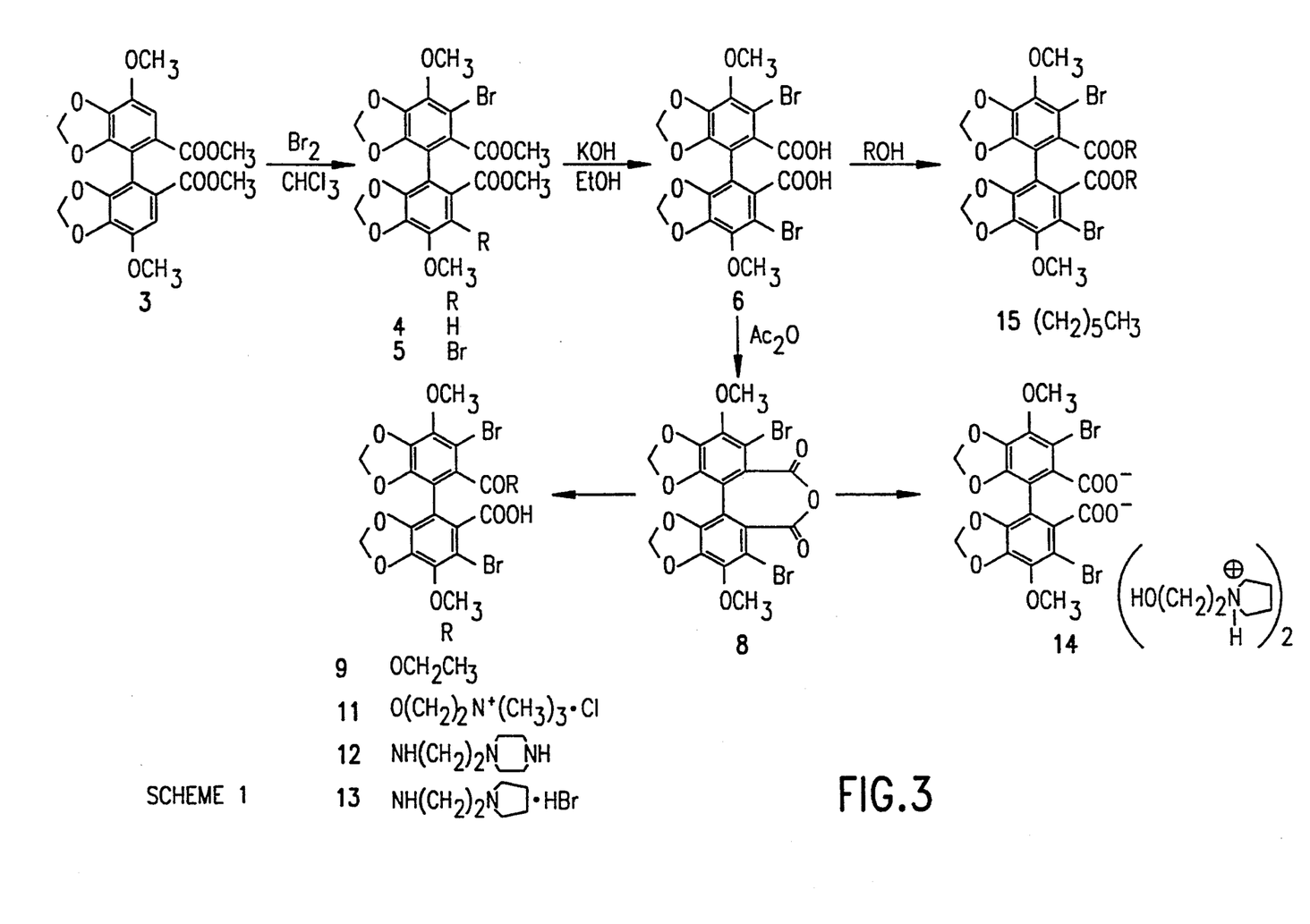
FIG. 3 is reaction scheme 1.

The inhibitory activity of compounds 4 and 5 against HIV-1 recombinant reverse transcriptase-associated reverse transcriptase (RT) activity was investigated as a mechanism of action study. As shown in Table II, these compounds exhibited template-primer dependent HIV-1 RT inhibitory activity. This type of inhibitory activity was also observed with other nonnucleoside HIV RT inhibitors [10-11]. The spectra of template-primer dependence are different between 4 and 5. In the case of 4, the enzyme was approximately 2 times more sensitive with Poly(rC)-olig(dG) as template-primer than with Poly(rA)-olig(dT). In contrast, the enzyme was about 6 times more sensitive to B with Poly(rA)-olig(dT) as template-primer than with Poly(rC)-olig(dG). Nevarapine, a non-nucleoside RT inhibitor, exerts more inhibitory activity using Poly(rC)-olig(dG) than with Poly(rA)-olig(dT).[10] Compounds 4 and 5 also demonstrated potent inhibitory effects against HIV-1 reverse-transcriptase-associated DNA polymerase activity using Poly(dA)-olig(dT) as template primer with $IC_{50}$ values of 0.056 and 0.048 μM, respectively. Comparison of the inhibitory activity against HIV-1 reverse transcriptase-associated reverse transcriptase and DNA polymerase activities using Poly(rA)-oligo(dT) and Poly(dA)-oligo(dT), respectively, as templateprimer revealed that compounds 4 and 5 possessed about 80 and 40 times more efficacy against DNA polymerase activity, respectively. Both compounds 4 and 5 could also inhibit HIV RT associated RNase H activity. This only occurred when Poly(rG)-poly(dC) was used as substrate and $Mn^{+2}$ (0.4 mM) was used as the divalent cation. Under these conditions, the two compounds had almost equal potency, as shown in FIG. 1. When Poly(rA)-poly(dT) was used as a substrate, or $Mg^{+2}$ was used as the divalent cation, no inhibition was observed. Since HIV-1 RT plays an important role in HIV replication, the potent inhibitory activity of compounds 4 and 5 against this enzyme catalyzed DNA-directed DNA synthesis might be related to their anti-HIV activity.

Data obtained by using chronically HIV-1 infected cell lines that are cultured with a test drug can give a sense of how these compounds may function in vivo if given to a latently HIV- infected individual. Therefore, compounds 4 and 5 were separately added for 72 hours to the chronically HIV-1 infected T cell line, ACH-2, and to the chronically HIV-1 infected promonocytic cell line, U1. There was no increase in the induction of virus expression from either cell line. Even when both chronically HIV-1 infected cell lines were cultured in the presence of a known virus inducer, such as the phorbol ester, PMA (phorbol 12-myristate 13-acetate), there was no alteration in the level of virus expression, as shown in Table III. Thus, compounds 4 and 5 did not increase or decrease virus expression from the chronically HIV-infected cells either when cultured alone or in the presence of PMA, respectively.

TABLE II

Inhibition of HIV-1 Reverse Transcriptase by Compounds 4 and 5

| | | | $IC_{50}$(μM)[c] | |
|---|---|---|---|---|
| Template-primer | Units used[a] | Relative rate[b] | 4 | 5 |
| RNA-dependent DNA polymerase associated activity | | | | |
| poly(rA)-olig(dT)$_{10}$ | $1 \times 10^{-3}$ | 100 | 4.5 ± 1.0 | 1.9 ± 0.9 |
| poly(rC)-olig(dG)$_{12-18}$ | $1 \times 10^{-3}$ | 36 | 2.2 ± 0.6 | 11 ± 0.5 |
| DNA-dependent DNA polymerase associated activity | | | | |
| poly(rA)-olig(dT)$^{10}$ | 0.05 | 10 | 0.056 ± 0.003 | 0.048 ± 0.004 |

[a]A unit is defined as the amount of enzyme required to incorporate 1 nmol of [$^3$H]dTMP into the poly(rA)-oligo(dT)$_{10}$ template in 1.0 min at 37° C.
[b]All the reaction rates were normalized to the reaction rate obtained using poly(rA)-olig(dT)$_{10}$.
[c]The values represent the mean ± standard deviation of three separate determinations.

TABLE III

Effect of Compounds 4 and 5 on Chronically Infected U1 Cells

| Sample Indentification* | p24 pg/mL | |
|---|---|---|
| | +Media | +PMA |
| U1 cells + 4 | | |
| 20 | 22 | 10,746 |
| 4 | 11 | 13,376 |
| 0.8 | 11 | 8,774 |
| 0.16 | 12 | 7,616 |
| 0.032 | 10 | 7,200 |
| 0.0064 | 7 | 8,314 |
| U1 cells + 5 | | |
| 20 | 15 | 10,131 |
| 4 | 16 | 10,598 |
| 0.8 | 14 | 11,482 |
| 0.16 | 13 | 9,850 |
| 0.032 | 15 | 8,320 |
| 0.0064 | 17 | 7,590 |
| U1 cells + AZT | | |
| 100 | 22 | 9,338 |
| 10 | 13 | 9,299 |
| 1 | 12 | 8,218 |
| 0.1 | 18 | 8,070 |
| U1 cells + media | 15 | 7,124 |

*Compound concentrations in μg/mL.

Testing Anti—HIV activity in vitro

The following are examples of methods which can be used to screen the compounds of the present invention for determining at least one therapeutic utility and/or mechanism of action as an anti-viral compound, such as an anti-HIV compound, without undue experimentation, based upon the teaching and guidance presented herein.

First, various concentrations of the compounds can be incubated with a chronically HIV-1 infected T cell line, e.g., ACH-2, and a chronically HIV-1 infected monocytic cell line, e.g., U1. These cell lines are useful in predicting if the compounds of the present invention could induce virus expression in vivo when given to an individual who is latently infected with HIV and not actively expressing virus. In addition, when these two cell lines are incubated with the phorbol ester, PMA, HIV-1 expression is increased. Since the compounds of the present invention can inhibit virus replication during an acute HIV-1 infection of H9 cells, it will be of interest to determine if these compounds can also suppress HIV-1 expression from these two chronically infected cell lines when they are stimulated with PMA.

Compounds of the present invention can be tested with other cell types (e.g., freshly isolated cells and/or cell lines) which are infected with HIV. Freshly isolated monocyte/macrophages and peripheral blood mononuclear cells (PBMCs) can be infected with a monotropic isolate of HIV-1, Ba-L and/or a laboratory isolate (e.g., IIIB) of HIV-1, respectively. In addition, virus suppression can be evaluated when a biphenyl derivative is added to acutely HIV-1 (IIIB isolate) infected monocytic cell line, U937, and/or the HIV-2 (d194 isolate) infected T cell line, HUT-78. These studies will determine if the suppressive effect of the biphenyl derivatives are specific to a particular cell phenotype or a virus isolate.

Other studies can be used to screen for the mechanism of action of compounds of the present invention by:

(a) Determining if the compound is capable of inactivating HIV-1 by culturing the compounds with HIV-1 for one hour before adding the virus to H9 cells;

(b) Determining if the compounds mechanism of action is competition with HIV for the same receptor (CD4) on the cell surface. This can be tested by adding HIV-1, biphenyl derivative and H9 cells together and then monitoring the amount of virus produced in the presence and absence of the biphenyl derivative;

(c) H9 cells can also be pretreated with the compounds to determine if the effect of the drug is on the cells or on the virus;

(d) Molecular biology studies, in which DNA and/or RNA levels can be measured in cells that had been treated with various concentrations of the compounds. This is preferred where negative results are obtained from one or more of methods (a)–(c). Both cellular and/or viral regulatory elements can be examined.

The compounds can also be tested in the presence of nucleoside analogs (AZT, ddI, ddC) or other accepted anti-HIV agents, to determine if the biphenyl derivatives are synergistic with any of these currently licensed anti-retroviral agents which can ultimately enhance their individual suppressive capability, especially at lower concentrations.

At least one compound of the present invention can be used for treatment of retroviral (e.g., HIV) infection either alone, or in combination with other modes of therapy known in the art. Such modes of therapy can include chemotherapy with drugs, such as, but not limited to, at least one of AZT, ddC, ddA, ddT, ddI, or any other anti-retroviral agents in combination with each other, or associated with a biologically based therapeutic, such as, for example, soluble CD4, antibodies to CD4, and conjugates of CD4 or anti-CD4, or as additionally presented herein.

Because the compounds of the present invention are relatively less toxic or substantially non-toxic to normal cells, their utility is not limited to the treatment of established retroviral infections. For example, a biphenyl derivative according to the present invention can be used in treating blood products, such as those maintained in blood banks. The nation's blood supply is currently tested for antibodies to HIV. However, the test is still imperfect and samples which yield negative tests can still contain HIV virus. Treating the blood and blood products with the compounds of the present invention can add an extra margin of safety by killing any retrovirus that may have gone undetected.

Pharmaceutical Compositions

Pharmaceutical compositions of the present invention can comprise at least one of the compounds of the present invention. Pharmaceutical compositions according to the present invention can also further comprise other anti-viral agents such as, but not limited to, AZT, ddI, 2'-β-fluoro-ddI, ddA, ddG, ddC, 2'-β-fluoro-ddC, d4T, AzddU, phosphonylmethoxyethyl-adenine, or soluble CD4, or immunomodulators, e.g., as presented below. For a review of therapeutic agents in HIV infections, see, e.g., Mitsuya et al., *FASEB J.* 5:2369–2381, 1991, which reference is hereby incorporated by reference.

Additional suitable antiviral agents for optimal use with at least one compound of the present invention can include, but are not limited to, AL-721 (lipid mixture, manufactured by Ethigen Corporation and Matrix Research laboratories; Amphotericin B methyl ester; Ampligen (mismatched RNA) developed by DuPont/HEM Research; anti-AIDS antibody (Nisshon Food); AS-101 (heavy metal based immunostimulant); AZT (azidothymidine/Retrovir/Zidovudine), manufactured by Burroughs Wellcome; Betaseron (β-interferon) manufactured by Triton Biosciences (Shell oil); butylated hydroxytoluene; Carrosyn (polymannoacetate) Castanospermine; Contracan (stearic acid derivative); Creme Pharmatex (containing benzalkonium chloride) manufactured by Pharmalec; CS-87 (5-unsubstituted derivative of Zidovudine); Cytovene (ganciclovir) manufactured by Syntex Corporation; ddC (dideoxycytidine) manufactured by Hoffmann-LaRoche, and other nucleoside analogues; dextran sulfate; D-penicillamine (3-mercapto-D-valine) manufactured by Carter-Wallace and Degussa Pharmaceutical; Foscarnet (trisodium phosphonoformate) manufactured by Astra AB; fusidic acid manufactured by Leo Lovens; glycyrrhizin (a constituent of licorice root); HPA-23 (ammonium-21-tungsto-9-antimonate) manufactured by Rhone-Poulenc Santé; human immunevirus antiviral developed by Porton Products International; Ornidyl (eflornithine) manufactured by Merrell-Dow; nonoxinol; pentamidine isethionate (PENTAM-300) manufactured by Lypho Med; Peptide T (octapeptide sequence) manufactured by Peninsula Laboratories; Phenytoin (Warner-Lambert); Ribavirin; Rifabutin (ansamycin) manufactured by Adria Laboratories; rsT4 (recombiniant soluble T4) manufactured by Biogen, Genentech and SmithKline Beecham; Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; Wellferon ($\infty$-interferon) manufactured by Burroughs Wellcome; Zovirex (acyclovir) manufactured by Burroughs Wellcome.

Pharmaceutical compositions of the present invention can also further comprise immunomodulators. Suitable immunomodulators for optional use with at least one compound of the present invention in accordance with the present invention can include, but are not limited to: ABPP (Bropririmine); Ampligen (mismatched RNA)DuPont/HEM Research; anti-human interferon-$\infty$- antibody (Advance Biotherapy and Concepts); anti-AIDS antibody (Nisshon Food); AS-101 (heavy metal based immunostimulate; ascorbic acid and derivatives thereof; interferon-$\beta$; Carrosyn (polymannoacetate); Ciamexon (Boehringer-Mannheim); cyclosporin; cimetidine; CL-246,738 (American Cyanamide); colony stimulating factors, including GM-CSF (Sandoz, Genetics Institute); dinitrochlorobenzene; interferon-$\infty$; inteferon-gamma; glucan; hyperimmune gamma-globulin (Bayer); IMREG-1 (leukocyte dialyzate) and IMREG-2 (IMREG Corp.); immuthiol (sodium diethylthiocarbamate) (Institut Merieux); interleukin-1 or interleukin-2 (Cetus Corporation; Hoffmann-LaRoche; Immunex); isoprinosine (inosine pranobex); Krestin(Sankyo); LC-9018 (Yakult); lentinan (Ajinomoto/Yamanouchi); LF-1695 (Fournier); methionine-enkaphalin (TNI Pharmaceuticals; Sigma Chemicals); Minophagen C; muramyl tripeptide, MTP-PE (Ciba-Geigy); naltrexone ("Trexan," DuPont); Neutropin; RNA immunomodulator (Nippon Shingaku); shosaikoto and ginseng; thymic humoral factor; TP-05 (Thymopentin, Ortho Pharmaceuticals); Thymosin factor 5 and Thymosin 1; Thymostimulin; TNF (Tumor necrosis factor) manufactured by Genentech; and vitamin B preparations.

Preferred antiviral agents that may be co-administered with compounds of the present invention include gamma globulin, amantadine, guanidine, hydroxybenzimidazole, interferon-$\alpha$, interferon-$\beta$, interferon-gamma, thiosemicarbazones, methisazone, rifampin, ribavirin, pyrimidine analogs, purine analogs, foscarnet, phosphonoacetic acid, acyclovir, dideoxynucleosides and ganciclovir.

Animal subjects that may be treated with compositions according to the present invention include mammals and birds.

The preferred animal subject of the present invention is a mammal. By the term "manual" is meant an individual belonging to the class Mammalia. The invention is particularly useful in the treatment to human patients.

The term "treating" means the administering to subjects a biphenyl derivative for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

In one preferred embodiment, at least one compound of the present invention is present in a single pharmaceutical composition.

Pharmaceutical compositions for administration according to the present invention can comprise at least one compound according to the present invention in a pharmaceutically acceptable form optionally combined with a pharmaceutically acceptable carrier. These compositions can be administered by any means that achieve their intended purposes. Amounts and regimens for the administration of a biphenyl derivative according to the present invention can be determined readily by those with ordinary skill in the clinical art of treating a retroviral pathology.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one compound according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 1 to about 100 mg/kg body weight of the active ingredient. The most preferred dosages comprise about 10 to about 100 mg/kg body weight.

Therapeutic administration can also include prior, concurrent, subsequent or adjunctlye administration of at least one additional compound according to the present invention or other therapeutic agent, such as an anti-viral or immune stimulating agent. In such an approach, the dosage of the second drug can be the same as or different from the dosage of the first therapeutic agent. Preferably, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or algininc acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills, tablets, including coated tables, elixirs, suspensions, syrups or inhalations and controlled release forms thereof.

Solid dosage forms in addition to those formulated for oral administration include rectal suppositories.

The compounds of the present invention can also be administered in the form of an implant when compounded with a biodegradable slow-release carrier. Alternatively, at least one compound of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, at least one compound may be administered in the form of an infusion solution or as a nasal inhalation or spray.

Having now generally described the invention, the same will be more readily understood through reference to the following examples, which are provided by way of illustration, and are not intended to be limiting of the present invention, unless specified.

Experimental

General Experimental Procedures

All melting points were determined on a Fischer-Johns melting point apparatus and are uncorrected. IR spectra were recorded on a Perkin-Elmer Model 1320 spectrometer. $^1$H NMR spectra were obtained using a Bruker AC-300 instrument with TMS or trimethylsilylpropionate-d4 (for $D_2O$ solvent) as an internal standard, and chemical shifts are given in δ (ppm). Mass spectra were measured on a VG Trio-1000. Elemental analyses were performed by Atlantic MicroLab Inc, Norcross, Ga. TLC was conducted on pre-coated Kieselgel 60 $F_{254}$ plates (0.20 mm, Merck), and spots were detected by UV illumination. EM Kieselgel 60 (70–230 mesh ASTM) was used for column chromatography. 0.0982N NaOH aqueous solution was purchased from Aldrich. All new compounds were characterized by $^1$H NMR and IR spectral analyses and elemental analyses.

Bromination of 4,4'-dimethoxy-5,6,5',6'-bimethylenedioxy-2,2'-dimethoxycarbonyl biphenyl, 4,4',5,5'-tetrakis-(benzyloxy)-6,6'-dimethoxy-2,2'-dimethoxycarbonyl biphenyl, and 4,4',5,5'-tetrakis(benzyloxy)-6,6'-dimethoxy-2,2'-dihydroxymethyl biphenyl. A solution of biphenyl (300–500 mg, 0.66–1 mmol) in chloroform(8–10 mL) was added dropwise to bromine (1 or 2 mol equivalent) in chloroform(5–8 mL) at 0°–5° C. The temperature was elevated to room temperature, and the mixture was stirred for 3 hours. The reaction mixture was poured into 20% sodium bisulfite aqueous solution (40–50 mL), which was extracted with chloroform. The chloroform layer was washed successively with 5% aqueous sodium bicarbonate, water, and brine, dried over sodium sulfate, and concentrated to dryness. The residue was crystallized from EtOH or purified by silica gel chromatography [hexane-ethyl acetate(7:1 or 4:1)] to yield mono- or dibromide.

3-Bromo-4,4'-dimethoxy-5,6,5',6'-bimethylenedioxy-2,2'-dimethoxycarbonyl biphenyl (4). Yield: 85%; mp 157°–159° C.; IR (KBr) 1720 (CO) cm$^{-1}$; $^1$H NMR(CDCl$_3$) δ3.62(s,3H,2'-COOCH$_3$)3.71 (s,3H,2-COOCH$_3$),3.97 (s,3H,4'-OCH$_s$) ,4.08 (s,3H,4-OCH$_3$),6.01, 6.04(m,4H in total, —OCH$_2$O—) ,7.33 (s,1H,H-3'). Anal. (C$_{20}$H$_{17}$O$_{10}$Br)C,H.

3,3'-Dibromo-4,4'-dimethoxy-5,6,5'6'-bimethylenedioxy-2,2'-dimethoxycarbonyl biphenyl (5). Yield:98%;mp 227°–229° C.;IR(KBr) 1710 (CO)$^{-1}$;$^1$H NMR(CDCl$_3$) δ3.71(s, 6H,2 and 2'-COOCH$_3$),4.08(s, 6H, 4 and 4 'OCH$_3$)6.01,6.03(each s, 2H-OCH$_2$O). Anal.(C$_{20}$H$_{16}$O$_{10}$Br$_2$)C,H,Br.

3,3'-Dibromo-4,4'-dimethoxy-5,6,5'6'-bimethylenedioxy-2,2'-dicarboxy biphenyl (6). A solution of 5 (500 mg, 0.87 mmol) in 40% potassium hydroxide aqueous solution (12 mL) and ethanol (20 mL) was refluxed for 4.5 hours. After cooling, the reaction mixture was neutralized with 37% hydrochloric acid. The resulting white precipitate was collected by filtration, washed with water, and dried to give the dicarboxylic acid (6) Yield: 90%;mp 230° C.(decomp); IR (KBr) 3000–2500 (COOH), 1690 (CO)cm$^{-1}$;$^1$H NMR(CDCl$_3$) δ4.03(s,6H,4,4'-OCH$_3$) 5.95, 6.0 (each s,2H, —OCH$_2$O—); MS m/z(%) 546 (M)$^+$(24),548(M+2)$^+$(48), 550(M+4)$^+$(23). Anal. (C$_{18}$H$_{12}$O$_{10}$Br$_2$)C,H,Br.

3,3'-Dibromo-4,4'-dimethoxy-5,6,5'6'-bimethylenedioxy-2,2'-dicarboxy biphenyl disodium salt (7). A solution of 6 (107.2 mg, 0.1963 mmol) in 0.0892N sodium hydroxide aqueous solution (4 mL, 0.3928 mmol) was kept standing at room temperature for 5 min. The mixture was concentrated in vacuo to yield the disodium salt (7) (114 mg) as a white solid. Yield: 98%; mp 153° C. (decomp); IR (KBr) 1585, 1380 (COO$^-$)cm$^{-1}$;$^1$H NMR (D$_2$O) δ3.93 (s,6H, 4,4'-OCH$_3$), 5.85, 5.90 (each s, 2H, —OCH$_2$O—); Anal. (C$_{18}$H$_{10}$O$_{10}$Br$_2$Na$_2$·2H$_2$O)C,H.

3,3'-Dibromo-4,4'-dimethoxy-5,6,5'6'-bimethylenedioxy biphenyl 2,2'-dicarboxylic anhydride (8). A solution of 6 (200 mg, 0.36 mmol) in acetic anhydride (3 mL) was refluxed for 24 hours with stirring. The mixture was concentrated in vacuo, and the residue was poured into water. The resulting off-white solid was collected by filtration and washed with water. Crystallization from ethyl acetate afforded 8 (179 mg) as a white solid. Yield 93%; mp 258° C.; IR 1800, 1770 (CO—O—CO) cm$^{-1}$; MS (%) m/z 528 (M)$^+$(31), 530 (M+2)$^+$(59), 532 (M+4)$^+$(29); $^1$H NMR (CDCl$_3$) δ4.11 (s,6H,4,4'-OCH$_3$), 6.06, 6.11 (each s, 2H, —OCH$_2$O—); Anal. (C$_{18}$H$_{10}$O$_9$Br$_2$)C,H,Br.

3,3'-Dibromo-4,4'-dimethoxy-5,6,5'6'-bimethylenedioxy-2-ethoxycarbonyl-2'-carboxy biphenyl (9). A solution of 8 (150 mg, 0.284 mmol) in ethanol (25 mL) was refluxed for 3 days with stirring. After removal of the solvent by evaporation, the residue was treated with 5% sodium hydroxide aqueous solution (20 mL), washed-with ethyl acetate, acidified with 10% aqueous hydrochloric acid, and extracted with ethyl acetate. The ethyl acetate layer was concentrated to dryness to furnish 9 (134 mg) as a white powder. Yield 84%; mp 239° C. (decomp.); IR (KBr) 3000–2500 (COOH), 1725 (CO) cm$^{-1}$;$^1$H NMR (DMSO-d$_6$) δ0.98 (t,J=7 Hz,3H, CH$_3$), 3.99, 4.00 (each s,3H,4,4'-OCH$_3$), 3.99–4.06(m,2H,OCH$_2$), 6.00–6.12(m,4H,2x-OCH$_2$O—); Anal. (C$_{20}$H$_{16}$O$_{10}$Br$_2$·5H$_2$O)C,H,Br.

3,3'-Dibromo-4,4'-dimethoxy-5,6,5'6'-bimethylenedioxy-2-ethoxycarbonyl-2'-carboxy biphenyl monosodium salt (10). A solution of 9 (56 mg, 0.0982 mmol) in 0.0982N sodium hydroxide aqueous solution (1 mL, 0.0982 mmol) was kept standing at room temperature for 5 minutes. Work up as for 7 gave the mono sodium salt (10) (52 mg) as a white solid. Yield: 90%; mp 227° C; IR (KBr) 1725 (CO) 1590, 1380 (COO$^-$)cm$^{-1}$;$^1$H NMR (D$_2$O) δ0.92 (t,J=7 Hz, 3H, CH$_3$), 3.93, 3.94 (each s,3h,4,4'-OCH$_3$), 4.09 (q,J=7 Hz,2H,OCH$_2$), 5.91 (m,4H,2x-OCH$_2$O—); Anal. (C$_{20}$H$_{15}$O$_{10}$Br$_2$Na)C,H,Br.

3,3'-Dibromo-4,4'-dimethoxy-5,6,5'6'-bimethylenedioxy-2-carboxy-2'-(β-N,N,N-trimethylamino)ethoxycarbonyl biphenyl chloride (11). A mixture of 8 (950 mg, 1.8 mmol) and choline chloride (250 mg, 1.8 mmol) in pyridine (3 mL) and DMF (2 mL) was stirred at room temperature for 5 days. The reaction mixture was concentrated to dryness to give an off-white solid. Crystallization from methanol gave 11 (1.02 g) as colorless prisms. Yield: 85%; mp 210° C.(decomp.);1H NMR (DMSO-d$_6$) δ3.11(br s,9H, N—CH$_3$) 3.40 (t,J=6 Hz,2H,N—CH$_2$), 3.82(m,2H,CH$_2$O), 3.97 (s,6H,4,4'-OCH$_3$), 5.96, 6.03 (each s, 2H, —OCH$_2$O—); Anal. (C$_{23}$H$_{24}$NO$_{10}$Br$_2$Cl)C,H.

3,3'-Dibromo-4,4'-dimethoxy-5,6,5'6'-bimethylenedioxy-2-carboxy-2'-(β-N-piperazine)ethylcarbonyl biphenyl (12). A mixture of 8 (528 mg, 1.1 mmol) and 1-(2-aminoethyl)piperazine (0.15 mL, 1.1 mmol) in benzene (25 mL) was stirred at room temperature for 24 hours. The reaction mixture was concentrated to dryness to give an off-white solid. Crystallization from methanol gave 12 (693 mg) as an off-white solid. Yield: 99%; mp 184(decomp)° C.;$^1$H NMR (CD$_3$OD) δ2.52 (4H,m,2xNHCH$_2$ of piperazine), 2.84 (2H, t,J=6 Hz,2'-CONHCH$_2$), 2.88 (6H,m,3xNCH$_2$), 3.98 (6H, s,4,4'-OCH$_3$), 5.86, 5.93 (each 2H, s, —OCH$_2$O—); Anal. (C$_{24}$H$_{25}$N$_3$O$_9$Br$_2$·2H$_2$O)C,H.

3,3'-Dibromo-4,4'-dimethoxy-5,6,5'6'-bimethylenedioxy-2-carboxy-2'-(β-N-pyrrolidinyl)ethylcarbonyl biphenyl hydrobromide (13). A mixture of 8 (150 mg, 0.284 mmol) and 1-(2-aminoethyl)piperazine (0.3 mL, 2.3 mmol) in benzene (10 mL) was stirred at room temperature for 1 hour. The reaction mixture was concentrated to dryness to give an off-white solid. Crystallization from ethanol containing 2% HBr yielded 13 (122 mg) as a white powder. Yield: 58%; mp 188° C.(decomp.); IR (KBr) 1710 (CO) 1610, 1590 (amide)cm$^{-1}$;$^1$H NMR (CD$_3$OD) δ2.04, 2.52, (each m,2H, CH$_2$), 3.16 (t,J=6 Hz,2H,2'-CONHCH$_2$), 3.41 (m,4H,2x NCH$_2$), 3.58(m,4H,2xNCH$_2$), 3.58(m,4H,2xNCH$_2$ of pyrrolidine), 4.00, 4.11 (each s, 3H,4,4'-OCH$_3$), 6.02, 6.08 (each s,2H, —OCH$_2$O—); Anal. (C$_{24}$H$_{25}$N$_2$O$_9$Br$_3$·H$_2$O)C, H.

3,3'-Dibromo-4,4'-dimethoxy-5,6,5'6'-bimethylenedioxy-2,2'-dicarboxy biphenyl di-1-(2-hydroxyethyl)pyrrolidinium salts (114). A mixture of 8 (528 mg, 1 mol) and 1-(2hydroxyethyl)pyrrolidine (0.2 mL) in pyridine (2 mL) and DMF (2 mL) was stirred at room temperature for 3 days. The reaction mixture was concentrated to dryness, and the residue was washed with acetone to yield 114 (363 mg) as a white solid. Yield: 49%; mp 149°–151° C.; IR (KBr) 1580, 1370 (COO$^{-1}$)cm$^{-1}$;$^1$H NMR (D$_2$O) δ1.95 (m,8H,4xCH$_2$ of pyrrolidine); 3.19 (t, J=5 Hz,4H,2xNCH$_2$), 3.26 (m, 8H,NCH$_2$ of pyrrolidine), 3.75 (t,J=5,Hz,4H, CH$_2$O), 3.93 (s,6H,4,4'-OCH$_3$), 5.83, 5.88 (each s,2H,OCH$_2$O). Anal. (C$_{30}$H$_{38}$N$_2$O$_{12}$Br)C,H.

3,3'-Dibromo-4,4'-dimethoxy-5,6,5'6'-bimethylenedioxy-2,2'-dihexanoxycarbonyl biphenyl (115). To a solution of 61 (273 mg, 0.5 mmol) in 1-hexanol (7 mL), thionyl chloride (2 mL) was added dropwise, and the mixture was refluxed for 3 days. The reaction mixture was concentrated to dryness, and the residue was subjected to silica gel chromatography. Elution with cyclohexane-ethyl acetate (4:1) gave 115 (134 mg) as a white powder. Yield: 37%, mp 115°–117° C.; IR (KBr) 2960, 2930, 2860 (CH$_2$), 1730 (CO) cm$^{-1}$;$^1$H NMR (CDCl$_3$) δ0.88 (t,J=6.5 Hz,6H,2xCH$_3$), 1.25(m, 12H, 6xCH$_2$), 1.47(m,4H,2xCH$_2$)4.07 (s,6H,4,4'-OCH$_3$), 4.07–4, 14 (m,4H,2xCH$_2$O), 5.99, 6.01 (each s,2H,OCH$_2$O). Anal. (C$_{30}$H$_{36}$O$_{10}$Br$_2$): C,H,Br.

2,2'-Dimethoxycarbonyl-3-bromo-4,4',5,5'-tetrakis-(benxyloxy)-6,6'-dimethoxybiphenyl (116). Yield: 85%; A white amorphous powder, $^1$H NMR (CDCl$_3$) δ3.51, 3.60, 3.73, 3.74 (each s,3H,OCH$_3$), 5.10–5.16 (m, 8H in total, PhCH$_2$O), 7.27–7.53 (m, 21H in total, aromatic-H and H-3'). Anal. (C$_{46}$H$_{41}$O$_{10}$Br)C,H.

2,2'-Dimethoxycarbonyl-3,3'-dibromo-4,4'5,5'-tetrakis-(benzyloxy)-6,6'-dimethoxy biphenyl (17). Yield: 90%; A white amorphous powder, $^1$H NMR (CDCl$_3$) δ 3.61, 3.79 (each s, 6H, OCH$_3$), 5.10–5.12 (m, 8H in total, PhCH$_2$O), 7.33–7.50 (m, 20H in total, aromatic-H). Anal. (C$_{46}$H$_{40}$O$_{10}$Br$_2$)C,H,Br.

2,2'-Dihydroxymethyl -3-bromo-4,4'5,5'-tetrakis(benzyloxy)-6,6'-dimethoxy biphenyl (18). Yield: 76%; A white amorphous powder, $^1$H NMR (CDCl$_3$) δ3.60, 3.67 (each s,3H,OCH$_3$), 4.09, 4.17, 4.25, 4.50 (each d,J=12 Hz, 1H, CH$_2$OH), 5.09–5.16 (m, 8H in total, PhCH$_2$O), 7.00 (s,1H, H-3'), 7.28–7.55 (m, 20H in total, aromatic-H). Anal. (C$_{44}$H$_{41}$O$_8$Br)C,H.

2,2'-Dihydroxymethyl-3,3'-dibromo-4,4'5,5'-tetrakis(benzyloxy)-6,6'-dimethoxy diphenyl (19). Yield: 78%; A white amorphous powder, $^1$H NMR (CDCl$_3$) δ3.61 (each s,3H, OCH$_3$, 4.50, 4.56 (each d, J=12 Hz, 1H, CH$_2$OH), 5.11 (s,4H,PhCH$_2$O), 5.13, 5.18 (each d, J=12 Hz,2H,PhCH$_2$O), 7.32–7.55 (m, 20H in total, aromatic-H). Anal. (C$_{44}$H$_{40}$O$_8$Br) C,H.

Methyl 2,3,4-trihydroxybenzoate (120)

Six grams (94 mmol) of 2,3,4-trihydroxybenzoic acid in 200 mL of methanol was refluxed in the presence of molecule sieves and 2 mL of sulfuric acid for five days. After the usual workup, 16.92 grams of methyl ester 111 was obtained in a 98% yield, m.p. 150°–152° C. (recrystallized from ethyl acetate).

IR cm$^{-1}$ 3345 (br, s, OH), 1645 (chelated ester C=O) and 1260 (ester C—O); $^1$H NMR δ ppm 3.92 (s, 3H, OCH$_3$), 5.46 and 5.79 (each 2, 1H, OH exchangeable with D$_2$O), 10.98 (s, 1H, chelated OH), 6.51 and 7.35 (each d, J=9 Hz, 1H, ArH). Anal (C$_8$H$_8$O$_5$) C,H.

Methyl 2, 3-dihydroxy-4-methoxybenzoate (121)

Compound 111 ( 18.4 g, 0.1 mol) in 5% aqueous borax solution was treated with 47 mL of methyl sulfate and 100 mL of 20% sodium hydroxide solution at 30° C. The mixture was stirred for five hours at room temperature. Then the mixture was cooled in an ice-bath and neutralized to pH 2 with hydroxyl chloride (37%). A precipitate occurred and was filtered and washed with water until the filtrate was neutral. The dried product 121 weighed 16.19 g (yield 86%) and was recrystallized from dilute aqueous ethanol as needles. m.p. 100°–101° C. IR cm$^{-1}$ 3330 and 3420 (OH), 1660 (chelated ester C=O) and 1255 (ester C—O); $^1$H NMR δ ppm 3.94 and 3.95 (each s, 3H, OCH$_3$), 5.51 (s, 1H, OH), 6.51 and 7.42 (each d, J=9 Hz, 1H, ArH), 10.84(s, 1H, chelated OH). Anal. (C$_9$H$_{10}$O$_5$)C,H.

Methyl 2,3-methylenedioxy-4-methoxybenzoate (122)

Compound 121 (16.12 g, 0.081 mol) was dissolved in 500 mL of DMF. Then 100 mL of methylene chloride and 26 g (0.464 mol) of potassium carbonate were added. The mixture was heated to 105° C. with vigorous stirring for 6 hours. The potassium carbonate was filtered and the DMF was removed in vacuo. The residue was poured into ice-water and let stand overnight. The precipitated product 122 was filtered and washed with water until neutral. The dried gray white solid weighed 15.60 g (yield 91%) and was recrystallized from methanol as brilliant long needles, m.p. 122°–124° C. IR cm$^{-1}$ 1710 (ester C=O); $^1$H NMR δ ppm 3.90 (s, 3H, OCH$_3$), 3.95 (s, 3H, ArOCH$_3$), 6.11 (s, 2H, OCH$_2$O), 6.57 and 7.45 (each d, J=9 Hz, 1H, ArH). Anal. (C$_{10}$H$_{10}$O$_5$)C, H.

Methyl 2,3-methylenedioxy-4-methoxy-5-bromobenzoate (123)

Compound 122 (5.56 g, 25.6 mmol) was dissolved in anhydrous chloroform. Bromine (4.5 g, 28.5 mmol) was added dropwise over 2 hours at 5°–8° C. Then the mixture was maintained for an additional 2 hours at the same temperature. After the usual workup, 6.9 g of white solid 123 was obtained (88% yield). m.p. 165°–6° C. (crystallized from ethyl acetate). IR cm$^{-1}$ 1710 (s, C=O), 1425, 1400 (s, C—O); MS m/z (%): 288 (M$^+$, 100), 290 (M+2, 96); $^1$H NMR δ ppm 3.91 (s, 3H, OCH$_3$), 4.14 (s, 3H, ArOCH$_3$), 6.10 (s, 2H, OCH$_2$O), 7.65 (s, 1H, 6-ArH); Anal. (C$_{10}$H$_9$O$_5$Br) C, H, Br.

Methyl 2,3-methylendioxy-4-methoxy-5-iodobenzoate (124)

A mixture of dry silver trifluoroacetate (442 mg, 2 mmol) and compound 122 (420 mg, 2 mmol) was placed in a reaction flask. Then a solution of iodine (506 mg, 2 mmol) in anhydrous methylene chlorate (8 mL) was added under reflux over a period of 2 hours. To this reaction mixture was added more silver trifluoracetate (40 mg) and iodine (59 mg) and reflux was continued until the starting material had disappeared on thin layer chromatography. The mixture was then filtered and the filtrate was concentrated. The resulting yellowish solid was crystallized from DMF as short needles (190 mg, yield 28%). m.p. 162°–4° C. IR cm$^{-1}$ 1706 (ester C=O), 1390 (C—O); $^1$H NMR δ ppm 3.90 (s, 3H, OCH$_3$), 4.13 (s, 3H, ArOCH$_3$), 6.10 (s, 2H, OCH$_2$O), 7.88 (s, 1H, ArH). Anal. (C$_{10}$H$_9$O$_5$I) C, H; I calcd. 37.90; found 37.80.

Methyl 2,3-methylenedioxy-4-methoxy-5- and -6-nitrobenzoate (125 and 126)

To a stirred suspension of compound 122 (442 mg, 2 mmol) in acetic anhydride (5 mL), concentrated nitric acid (1 mL) was added dropwise over a period of 20 minutes. The reaction temperature was maintained at 10°–22° C. The reaction mixture was stirred for an additional 30 minutes and then was poured into ice water. A yellowish solid (437 mg) was collected. Total yield was 86%. It was separated by silica gel column chromatography to afford the 5-nitro compound 125 and 6-nitro compound 126 (ratio 1:10). 125: m.p. 162°–4° C. $^1$H NMR δ ppm 3.93 (s, 3H, OCH$_3$), 4.19 (s, 3H, ArOCH$_3$), 6.23 (s, 2H, OCH$_2$O), 8.11 (s, 1H, 6-ArH). Anal. (C$_{10}$H$_9$NO$_7$) C, H, N. 126: m.p. 145°–7° C. (yellowish needles from ethyl acetate); IR cm$^{-1}$ 1735 (s, C=O); MS m/z (%): 255 (M$^+$, 100); $^1$H NMR (CD$_3$COCD$_3$) δ ppm 3.86 (s, 3H, OCH$_3$), 4.04 (s, 3H, ArOCH$_3$), 6.31 (s, 2H, OCH$_2$O), 7.48 (s, 1H, 5-ArH). Anal. (C$_{10}$H$_9$NO$_7$) C, H, N.

Methyl 2,3-methylenedioxy-4-methoxy-6- and 5-aminobenzoate (127 and 128)

A solution of 126 (225 mg, 1 mmol) in ethanol (10 ml) and ethyl acetate (5 mL) was placed in a reaction bottle and 10% palladium carbon catalyst (54 mg) was added. Hydrogen was added under vigorous stirring at room temperature and 1 atmosphere pressure for 4 hours. Then the catalyst was filtered and solvent was removed in vacuo. The amino compound 128 (148 mg) was thus obtained in a 93% yield. m.p. 163°–4° C. IR cm$^{-1}$ 3450, 3320 (NH), 1665 (chelated ester C=O); MS m/z (%): 225 (M+, 100); $^1$H NMR (CD$_3$COCD$_3$) δ ppm 3.77 (s, 3H, OCH$_3$), 3.82 (s, 3H, ArOCH$_3$), 5.88 (s, 3H, OCH$_2$O), 6.02 (s, 1H, 5-ArH), 6.21 (br.S, 1H, NH exchangeable with D$_2$O), 10.72 (s, 1H, chelated NH). Anal. (C$_{10}$H$_{11}$O$_5$N) C, H, N. According to the above procedure, 129 was obtained from 125 in a 84% yield. m.p. 139°–40° C. $^1$H NMR δ ppm 3.67 (br.s, 2H, NH$_2$), 3.89 (s, 3H, OCH$_3$), 4.09 (s, 3H, ArOCH$_3$), 5.99 (s, 2H, OCH$_2$O), 6.78 (s, 1H, 6-ArH). Anal. (C$_{10}$H$_{11}$O$_5$N•½H$_2$O) C, H.

Methyl 2,3-methylendioxy-4-method-6-iodobenzoate (128)

A suspension of compound 127 (400, 1.78 mmol) in 20% sulfuric acid (2 mL) was cooled to 0°–5° C. and then a solution of sodium nitrite (127 mg, 1.78 mmol) in water (4 mL) was added. After the diazonium salt was formed, a cooled solution of potassium iodide (332 mg, 2 mmol) in H$_2$O (2 mL) was added with evolution of a gas. Copper powder (340 mg) was added and the reaction mixture was stirred for 20 minutes, then heated on a water bath to 80°–90° C. for 1 hour. Nitrogen evolved vigorously. When the reaction subsided, the mixture was extracted with chloroform. A deep red oil (2.43 g) was obtained and was purified by silical gel column chromatography (eluent hexane: chloroform=4:1) giving 150 mg of 128 (25% yield). m.p. 146°–7° C. (white solid). IR cm$^{-1}$ 1705 (C=O), 1285 and 1265 (s, C—O); MS m/z (%): 336 (M$^+$, 100); $^1$H NMR δ ppm 3.93 (s, 6H, 2xOCH$_3$), 6.07 (s, 2H, OCH$_2$O), 7.11 (s, 1H, ArH). Anal. (C$_{10}$H$_9$O$_5$I) C, H.

5,5'-Dimethoxy-3,4,3'4'-bismethylenedioxy-2,2'-dimethoxycarbonyl biphenyl (ω-DDB) (116)

Method A (Ullmann reaction): A mixture of compound 128 (1 g, 2.85 mol), activated copper powder (1 g) an anhydrous DMF (3.5 mL) was heated to reflux for 2.5 hours under vigorous stirring. After cooling to 100° C., it was poured into ice water and the precipitate was collected and chromatographed on alumina. Elution with hexane then hexane-chloroform afforded ω-DDB 116 (280 mg, 44% yield). m.p. 253°–5° C. IR cm$^{-1}$ 1730 (C=O), 1175 and 1150 (s, C—O); MS m/z(%): 418 (M$^+$, 100); $^1$H NMR δ ppm 3.68 (s, 6H, 2xOCH$_3$), 3.92 (s, 6H, 2xOCH$_3$), 6.13 (s, 4H, 2xOCH$_2$O), 6.36 (s, 2H, 2xArH). Anal. (C$_{20}$H$_{18}$O$_{10}$) C, H.

Method B: Copper (II) sulfate (1.25 g) was dissolved in 5 mL of water containing 2.5 mL ammonium hydroxide(conc.). The mixture was cooled in an ice-bath to below 10° C. and solution of 0.4 g hydroxylamine chloride in 2 mL water and 1 mL sodium hydroxide (6N) was added. The diazonium salt of compound 127 (225 mg), prepared according to the above method given above in the synthesis of 128, was slowly added into the copper (II) solution and remained at <10° C. with vigorous stirring. The blue color faded gradually. The mixture was heated to 80°–90° C. for a few minutes, then cooled at room temperature and neutralized with hydrochloric acid to pH 2–3. After the usual work up, 86 mg of pure compound 116 was obtained (41% yield).

2,2'-Dimethoxy-3,4,3'4'-bismethylenedioxy-5,5'-dimethoxycarbonyl biphenyl (δ-DDB) (117)

Method A (Ullmann reaction): Compound 117 was obtained from 123 in a 10% yield using method A given above for 116. m.p. 195°–200° C. IR cm$^{-1}$ 1700 (s, ester C=O), 1430, 1270 and 1210 (s, C—O); MS m/z(%): 418 (M$^+$, 100); $^1$HNMR δ ppm 3.90 and 4.00 (each s, 3H, OCH$_3$), 6.13 (s, 4H, OCH$_2$O), 7.30 (s, 2H, ArH). Anal. (C$_{20}$H$_{18}$O$_{10}$), C, H.

Method B: Compound 117 was obtained in a 40% yield from 129 using method B as given for 116.

Bromination of biphenyl derivatives

A biphenyl compound in chloroform was dropped slowly into two molar equivalents of bromine at 0°–5° C. The mixture was stirred at room temperature for 3 hours and poured with stirring into ice-water containing sodium disulfide until the orange-red color faded completely. The organic phase was separated and washed successively with aqueous sodium bicarbonate, water and brine, then dried over sodium sulfate. The organic solvent was removed in vacuo. The crude produce was purified by crystallization.

3,3'-Dibromo-6,6'-dimethoxy-4,5,4',5'-bimethylenedioxy-2,2'-dimethoxycarbonyl biphenyl (118)

Obtained in a 87% yield from 123. Crystals from chloroform and methanol (2:1); m.p. 181°–2° C.; MS m/z(%): 574 (M$^+$, 48), 576 (M+2, 100), 578 (M+4, 51); $^1$HNMR δ ppm 3.67 (s, 6H, 2,2'-OCH$_3$), 3.90 (s, 6H, 6,6'-OCH$_3$), 6.12 (s, 4H, 2xOCH$_2$O), Anal. (C$_{20}$H$_{16}$O$_{10}$Br$_2$) C, H.

3,3'-Dibromo-4,6'-dimethoxy-5,6,4'5'-bimethylenedioxy-2,2'-dimethoxycarbonyl biphenyl (119)

Obtained in a 82% yield from 115. Crystals from chloroform and methanol (2:1). m.p. 166°–9° C. MS m/z(%): 574 (M$^+$, 45), 576 (M+2, 90), 578 (M+4, 59 (100); $^1$HNMR δ ppm 3.68 and 3.69 (each s, 3H, 2,2'-OCH$_3$), 3.91 (s, 3H, 4-OCH$_3$), 4.09 (s, 3H, 6'-OCH$_3$), 5.98–6.08 (m, 4H, 2xOCH$_2$O). Anal. (C$_{20}$H$_{16}$O$_{10}$Br$_2$) C, H. 6,6'-Dibromo-5,5'-dimethoxy-3,4,3'4'-bimethylenedioxy-2,2'-dimethoxycarbonyl biphenyl (110)

Obtained in 98% yield from 116. m.p. 187°–8° C. (crystals from ethyl acetate). MS m/z(%): (M$^+$, 50), 576 (M+2, 100), 578 (M+4, 50); 1H NMR δ ppm 3.69 (s, 6H, 2,2'-OCH$_3$), 4.14 (s, 6H, 5,5'-OCH$_3$), 6.10 and 6.13 (each s, 4H, 2xOCH$_2$O). Anal. (C$_{20}$H$_{16}$O$_{10}$Br$_2$·½H$_2$O) C, H.

| | | ELEMENTAL ANALYSES | | | | | |
|---|---|---|---|---|---|---|---|
| | | Calculated | | | Found | | |
| | | C | H | N | C | H | N |
| 61 | C$_{20}$H$_{18}$O$_{10}$ | 57.42 | 4.34 | | 57.21 | 4.59 | |
| 71 | C$_{20}$H$_{18}$O$_{10}$ | 57.42 | 4.34 | | 57.32 | 4.34 | |
| 81 | C$_{20}$H$_{16}$O$_{10}$Br$_2$ | 41.82 | 2.81 | | 41.84 | 2.94 | |
| 91 | C$_{20}$H$_{16}$O$_{10}$Br$_2$ | 41.82 | 2.81 | | 41.78 | 2.91 | |
| 110 | C$_{20}$H$_{16}$O$_{10}$Br$_2$·½H$_2$O | 41.12 | 2.92 | | 41.27 | 2.79 | |
| 111 | C$_8$H$_8$O$_5$ | 52.16 | 4.38 | | 51.99 | 4.34 | |
| 112 | C$_9$H$_{10}$O$_5$ | 54.53 | 5.09 | | 54.51 | 5.09 | |
| 113 | C$_{10}$H$_{10}$O$_5$ | 57.13 | 4.80 | | 57.01 | 4.80 | |
| 114 | C$_{10}$H$_9$O$_5$Br | 41.67 | 3.15 | | 41.65 | 3.13 | |
| 116 | C$_{10}$H$_9$O$_7$N | 47.05 | 3.56 | 5.49 | 47.21 | 3.59 | 5.52 |
| 117 | C$_{10}$H$_9$O$_7$N | 47.05 | 3.56 | 5.49 | 47.22 | 3.57 | 5.42 |
| 118 | C$_{10}$H$_{11}$O$_5$N | 53.32 | 4.93 | 6.22 | 53.49 | 5.03 | 5.84 |
| 119 | C$_{10}$H$_9$O$_5$I | 35.72 | 2.70 | | 35.86 | 2.79 | |
| 120 | C$_{10}$H$_{11}$O$_5$N·½H$_2$O | 47.61 | 5.60 | | 47.30 | 5.43 | |

HIV Growth Inhibition Assay.

The H9 T cell line was maintained in continuous culture with complete medium (RPMI and 10% fetal calf serum) at 5% $CO_2$ and 37° C. and was used in experiments only when in log phase of growth. The cells were incubated with HIV-1 (IIIB isolate, $TCID_{50} 10^4 IU/mL$, at a multiplicity of infection of 0.1–0.01 IU/cell) for 1 hour at 37° C. and 5% $CO_2$. The cells then were washed thoroughly to remove unabsorbed virions and resuspended at $4 \times 10^5$ cells/mL in complete medium. Aliquots (1 mL) were placed in wells of 24-well culture plates containing an equal volume of test compound (diluted in the culture medium). After a four day incubation at 37° C., cell density of uninfected cultures was determined by counting cells in a Coulter counter to assess toxicity of the test compound. A p24 antigen ELISA assay was used to determine the level of virus released in the medium of the HIV-infected cultures. The p24 antigen assay uses an HIV-1 anti-p24 specific monoclonal antibody as the capture antibody coated on 96 well plates. Following a sample incubation period, rabbit serum containing antibodies for HIV-1 p24 is used to tag any p24 "captured" onto the microtiter well surface. Peroxidase conjugated goat anti-rabbit serum is then used to tag HIV-1 p24 specific rabbit antibodies that have complexed with captured p24. The presence of p24 in test samples is then revealed by addition of substrate. The cut-off for the p24 ELISA assay is 12.5 pg/mL. P24 in the culture medium was quantitated against a standard curve containing known amounts of p24. The effective ($EC_{50}$) and inhibitory concentrations (for anti-HIV activity and cytotoxicity, respectively) were determined.

Preparation of HIV-1 Reverse Transcriptase.

HIV-1 reverse transcriptase was purified using Escherichia coli JM 109 containing pKRT 2 kindly provided by W. C. Summers (Yale University).

Enzyme Assay. All reactions were developed in a total volume of 50 μl containing 50 mMTris HCl pH 7.8, 2 mM $MgCl_2$, 100 μg/mL nuclease-free BSA, 1 mM dithiothreitol, 0.5 O.D.$_{260}$ unit/mL of template-primer, and 330 nM of [$^3$H]dNTP according to Cheng et al.

Chronically HIV-infected cell line.

HIV-1 chronically infected T cell line, ACH-2, [15] and HIV-1 chronically infected promonocytic cell line, U1 [16] were continuously maintained in RPMI1640 with 10% fetal calf serum (FCS). For experiments, the cell lines were only used in log-phase of growth. Cells ($1 \times 10^6$ cells/well) and either various concentrations of 4,5, AZT or media alone were added to 24-well plates in the presence or absence of PMA ($10^{-8}$M). After 72 hours at 37° C. and 5% $CO_2$, an aliquot of the cell-free supernatants was collected and analyzed for p24 antigen by ELISA.

| | | Elemental Analyses | | | | | |
|---|---|---|---|---|---|---|---|
| | | Calculated | | | Found | | |
| | | C | H | Br | C | H | Br |
| 4 | $C_{20}H_{17}O_{10}Br$ | 48.31 | 3.45 | | 47.97 | 3.38 | |
| 5 | $C_{20}H_{16}O_{10}Br_2$ | 41.69 | 2.80 | 27.74 | 41.66 | 2.83 | 27.67 |
| 6 | $C_{18}H_{12}O_{10}Br_2$ | 39.45 | 2.21 | 29.16 | 39.39 | 2.24 | 29.07 |
| 7 | $C_{18}H_{10}O_{10}Br_2Na_2 \cdot 2H_2O$ | 34.42 | 2.25 | | 34.15 | 2.23 | |
| 8 | $C_{18}H_{10}O_9Br_2$ | 40.79 | 1.89 | 30.15 | 40.80 | 1.93 | 30.09 |
| 9 | $C_{20}H_{16}O_{10}Br_2 \cdot 1.5H_2O$ | 39.83 | 3.18 | | 39.83 | 2.78 | |
| 10 | $C_{20}H_{15}O_{10}Br_2Na$ | 40.16 | 2.53 | | 39.90 | 2.54 | |
| 11 | $C_{23}H_{24}NO_{10}Br_2Cl$ | 41.25 | 3.61 | | 40.96 | 3.88 | |
| 12 | $C_{24}H_{25}N_3O_9Br_2 \cdot 2H_2O$ | 41.46 | 4.20 | | 41.12 | 4.42 | |
| 13 | $C_{24}H_{25}N_2O_9Br_3 \cdot 0.5H_2O$ | 39.21 | 3.70 | | 39.24 | 3.56 | |
| 14 | $C_{30}H_{38}N_2O_{12}Br_2$ | 46.29 | 4.92 | | 46.11 | 5.25 | |
| 15 | $C_{30}H_{36}O_{10}Br_2$ | 50.30 | 5.06 | 22.31 | 50.53 | 5.11 | 22.14 |
| 16 | $C_{46}H_{41}O_{10}Br$ | 66.27 | 4.96 | | 66.10 | 5.02 | |
| 17 | $C_{46}H_{40}O_{10}Br_2$ | 60.54 | 4.42 | 17.51 | 60.71 | 4.49 | 17.66 |
| 18 | $C_{44}H_{41}O_8Br$ | 67.95 | 5.31 | | 68.17 | 5.37 | |
| 19 | $C_{44}H_{40}O_8Br_2$ | 61.70 | 4.71 | | 61.66 | 4.74 | |

All references cited herein, including journal articles or abstracts, published or corresponding U.S. or foreign patent applications, issued U.S. or foreign patents, or any other references, are hereby incorporated in their entirety by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based upon the teaching and guidance presented herein. It is to be understood that the phraseology or terminology herein is for the purposes of description and not of limitation, such that the terminology or phraseology of the present specification is to be interpreted by the skilled artisan in light of the teachings and guidance presented herein, in combination with the knowledge of one or ordinary skill in the art.

What is claimed is:

1. A compound having one of the formulae:

wherein
$R^1$ and $R^2$ are independently hydrogen or bromine;
$R^3$ and $R^4$ are independently one of hydroxy, $C_{1-6}$ alkoxy, $-O(CH_2)_2N^+(CH_3)_3Cl^-$, provided that (a) $R^1$ and $R^2$ are not both hydrogen, and (b) when $R^3$ and $R^4$ are both methoxy, then $R^1$ and $R^2$ are not both bromine.

2. A compound according to claim 1, wherein $R^3$ and $R^4$ are each methoxy.

3. A compound according to claim 2, wherein $R^1$ is Br and $R^2$ is hydrogen.

4. A compound according to claim 3, which is 3-bromo-4,4'-dimethoxy-5,6,5',6'-bimethylenedioxy-2,2'-dimethoxycarbonyl biphenyl.

5. A pharmaceutical composition, comprising as active ingredients:

(a) a compound having one of the formulae:

wherein
$R^1$ and $R^2$ are independently hydrogen or bromine, with the proviso that $R^1$ and $R^2$ cannot both be hydrogen; and
$R^3$ and $R^4$ are independently one of hydroxy, $C_{1-6}$ alkoxy, $-O(CH_2)_2N^+(CH_3)_3Cl^-$, (b) at least one drug selected from the group consisting of anti-viral agents and immunostimulating agents.

6. A pharmaceutical composition according to claim 5, wherein said at least one drug is at least one anti-viral agent selected from the group consisting of gamma globulin, amantadine, guanidine, hydroxybenzimidazole, interferon-α, interferon-β, interferon-gamma, thiosemicarbazones, methisazone, rifampin, ribavirin, pyrimidine analogues, purine analogues, foscarnet, phosphonoacetic acid, acydovir, dideoxynucleosides and ganciclovir.

7. A pharmaceutical composition comprising at least one compound according to claim 1 as an active ingredient, and a pharmaceutically acceptable carrier.

8. A method for inhibiting a retroviral infection in cells or tissues of an animal, comprising administering a retroviral inhibiting effective amount of a compound having one of the formulae:

wherein
$R^1$ and $R^2$ are independently hydrogen or bromine, with the proviso that $R^1$ and $R^2$ cannot both be hydrogen; and
$R^3$ and $R^4$ are independently one of hydroxy, $C_{1-6}$ alkoxy, $-O(CH_2)_2N^+(CH_3)_3Cl^-$, 9. The method of claim 8, wherein $R^3$ and $R^4$ are each methoxy.

10. The method of claim 9, wherein $R^1$ is Br and $R^2$ is hydrogen.

11. The method of claim 9, wherein $R^1$ and $R^2$ are both Br.

12. The method of claim 8, wherein said compound is administered in an amount ranging from about 1 to about 100 mg/kg body weight.

13. The method of claim 12, wherein said compound is administered in an amount ranging from about 10 to about 100 mg/kg body weight.

14. The method of claim 8, wherein said animal is a mammal or bird.

15. The method of claim 14, wherein said animal is a human.

16. A method of ameliorating a retroviral related pathology in a patient suffering therefrom, comprising administering to said patient a retroviral inhibiting effective amount of a compound of the formula:

wherein

R¹ and R² are independently hydrogen or bromine, with the proviso that R¹ and R² cannot both be hydrogen; and R³ and R⁴ are independently one of hydroxy, $C_{1-6}$ alkoxy, $-O(CH_2)_2N^+(CH_3)_3Cl^-$, 17. The method of claim 16, wherein said retroviral related pathology is an HIV infection.

18. The method of claim 16, wherein R³ and R⁴ are each methoxy.

19. The method of claim 18, wherein R¹ is Br and R² is hydrogen.

20. The method of claim 18, wherein R¹ and R² are both Br.

* * * * *